United States Patent [19]

Morse et al.

[11] Patent Number: 5,219,328
[45] Date of Patent: Jun. 15, 1993

[54] FIBRIN SEALANT DELIVERY METHOD

[75] Inventors: Brenda S. Morse, Chamblee; A. Denise Turner, Dunwoody; Robert T. McNally, Marietta, all of Ga.

[73] Assignee: CryoLife, Inc., Marietta, Ga.

[21] Appl. No.: 460,379

[22] Filed: Jan. 3, 1990

[51] Int. Cl.$^5$ .................... A61M 31/00; A61M 35/00
[52] U.S. Cl. ........................ 604/49; 604/54; 604/56; 604/290; 606/214
[58] Field of Search .............. 604/46, 49, 56, 290; 128/897, 898; 424/529–531; 602/48–50; 606/214

[56] References Cited

U.S. PATENT DOCUMENTS

| | | | |
|---|---|---|---|
| 2,492,458 | 12/1949 | Berry | 602/50 |
| 2,533,004 | 12/1950 | Ferry et al. | 602/50 |
| 3,723,244 | 3/1973 | Breillatt, Jr. | 602/50 |
| 4,265,233 | 5/1981 | Sugitachi et al. | 602/50 |
| 4,359,049 | 11/1982 | Redl et al. | 604/191 |
| 4,359,463 | 11/1982 | Rock | 424/530 |
| 4,377,572 | 3/1983 | Schwarz et al. | 514/2 |
| 4,427,651 | 1/1984 | Stroetmann | 530/387 |
| 4,442,655 | 4/1984 | Stroetmann | 424/445 |
| 4,453,939 | 6/1984 | Zimmerman . | |
| 4,627,879 | 12/1986 | Rose . | |
| 4,631,055 | 12/1986 | Redl et al. | 604/191 |
| 4,655,211 | 4/1987 | Sakamoto et al. | 602/50 |
| 4,696,812 | 9/1987 | Silbering et al. | 602/50 |
| 4,735,616 | 4/1988 | Eibl et al. | 604/191 |
| 4,902,281 | 2/1990 | Avoy | 604/201 |

FOREIGN PATENT DOCUMENTS

3622642A1 of 0000 Fed. Rep. of Germany .

OTHER PUBLICATIONS

Haberli et al. (1987) Propolymers 26:27–43.
Dresdale et al., Hemostatic Effectiveness of Fibrin Glue Derived from Single-Donor Fres Frozen Plasma, Ann. Thorac. Surg., 40:385 (1985).
Lupinetti et al., Cryoprecipitate-topical thrombin gel: Initial experience in patients undergoing cardiac operations, J. Thorac. Cardiovasc. Surg., 90:502 (1985).
Carr et al., Influence of Ca2+ on the Structure of Reptilase-derived and Thrombin-derived fibrin gels, Biochem. J. 293:513 (1986).
Kaminski et al., Studies on the Mechanism of Thrombin, J. Biol. Chem. 258:10530 (1983).
Turner et al., Photochemical Activation of Acylated-Thrombin, J. Am. Chem. Soc. 109:1274–1275 (1987).
Turner et al., Photoreactivation of Irreversibly Inhibited Serine Proteases, J. Am. Chem. Soc. 110:244–250 (1988).
Porter et al., Acyl Thrombin Photochemistry: Kinetics for Deacylation of Enzyme Cinnamate Geometric Isomers, J. Am. Chem. Soc. 111:7616–7618 (1989).
Laki, The Polymerization of Proteins: the Action of Thrombin on Fibrinogen, Arch Biochem. Biophys., 32:317–324 (1951).
David E. Metzler, "Biochemistry, The Chemical Reactions of Living Cells", Academic Press, Inc. N.Y. 1977 pp. 330–331.
Arthur C. Guyton, "Physiology of the Human Body", W. B. Saunders Company, Philadelphia 1979 pp. 69–75.

*Primary Examiner*—C. Fred Rosenbaum
*Assistant Examiner*—Mark Bockelman
*Attorney, Agent, or Firm*—Cushman, Darby & Cushman

[57] ABSTRACT

The present invention relates to a method for the formulation of fibrin sealant in a single delivery system. The method involves mixing a fibrinogen/Factor XIII precipitate solution with thrombin under conditions such that thrombin clotting activity is inhibited and said mixture is applied to a body site under conditions which activate the thrombin to convert fibrinogen into fibrin sealant. A single device, syringe or container, can be used to apply the fibrin sealant formulation.

6 Claims, No Drawings

FIBRIN SEALANT DELIVERY METHOD

BACKGROUND OF THE INVENTION

1. Technical Field

The present invention relates to a method of fibrin sealant preparation and delivery, which permits use of a single delivery device The method may be used for autologous, single-donor, pooleddonor or cell culture-derived fibrin sealant for various human and veterinary surgical procedures. The invention further relates to a kit suitable for use in such a method

2. Background Information

The blood coagulation system is a complex series of proteins and factors which are activated sequentially to produce a fibrin gel or clot. In the final stages of the process, fibrinogen is cleaved by thrombin to generate fibrin monomer, which rapidly polymerizes and is cross-linked by activated Factor XIII to form a fibrin matrix Preparations of human coagulation factors, including fibrinogen and thrombin, have been used extensively in surgery over the last ten years (Schlag et al (eds), Fibrin Sealant in Operative Medicine, vol 1-7, Springer-Verlag, Heidelberg). These biological fibrin sealants promote hemostasis and wound healing by sealing leakage from tissues, sutures, staples, and prostheses, and are particularly useful during open heart surgery in heparinized patients. The sealants also have use as an adhesive for the bonding of tissues and they reduce the amount of blood required for transfusions by controlling intraoperative bleeding. Their effectiveness is reflected in the extensive range of surgical applications for which they have been used, including cardiovascular surgery, plastic surgery, orthopedics, urology, obstetrics and gynecology, dentistry, maxillofacial and ophthalmic surgery.

Fibrin sealant products prepared from pooled human plasma fibrinogen/Factor XIII are available commercially in Europe (Tissucol/Tisseel, Immuno AG, Vienna, Austria and Beriplast P, Hoechst, West Germany) but such products have not received U.S. Food and Drug Administration approval As an alternative, some hospitals are preparing fibrin sealant in-house using the patient's own blood (autologous) or single-donor (homologous) plasma as a source of fibrinogen and Factor XIII.

The plasma fibrinogen/Factor XIII component of fibrin sealant is typically prepared by freezing plasma at a temperature below −20° C. overnight, slowly thawing the material at 0–4° C., centrifuging, and transferring the cryoprecipitate to a syringe or spray container (Dresdale et al, Ann. Thorac. Surg. 40:385 1985; and U.S. Pat. No. 4,627,879). The thrombin component, usually purified from bovine plasma, can be obtained commercially and is typically prepared in a separate syringe or spray container. In use, the two solutions are delivered simultaneously or alternately to generate fibrin sealant at the site of the wound; alternatively, the sealant is applied to a collagen matrix (e.g. Gelfoam or Avitene) and then pressed against the site (Lupinetti et al, J. Thorac Cardiovasc. Surg. 90:502 1985; and U.S. Pat. No. 4,453,939).

Generation of fibrin sealant at the wound site can be effected using a two syringe system. Such a system is, however, unsatisfactory due to the awkwardness of filling and manipulating the delivery devices at the wound site In addition, the syringe system is accompanied by problems of inadequate mixing of the two solutions, resulting in the formation of a weak clot. Alternatively, the two syringes can be placed into a holder designed such that the solutions are permitted to mix before entering the needle (U.S. Pat. Nos. 4,735,616, 4,359,049, and 4,631,055). Although the strength of the clot obtained using this method is reproducible, the needle frequently clogs and must repeatedly be replaced.

In view of the problems inherent in the methodologies currently available for delivering fibrin sealant, the need for a simple, reproducible technique is clear. Such a technique must be convenient to use and must result in the formation, at a specific site, of a clot of appropriate strength. Such a delivery technique is provided by the invention disclosed herein.

SUMMARY OF THE INVENTION

It is a general object of the present invention to provide a method of forming a fibrin sealant from blood coagulation components that overcomes the problems associated with methods known in the art.

It is a specific object of the invention to provide a method of delivering fibrin sealant to a wound site, in which method a fibrinogen/Factor XIII-enriched precipitate (or a fibrinogen/Factor XIII mixture) and thrombin are mixed together under conditions such that clotting is prevented until such time as sealant formation is desired.

It is a further object of the invention to provide a kit suitable for use in the above-described method.

A more complete appreciation of the present invention and the advantages thereof will be readily understood by one skilled in the art from a reading of the description that follows.

In one embodiment, the present invention relates to a method of effecting the formation of fibrin sealant at a body site. The method comprises: i) mixing, in a container means, an aqueous solution comprising fibrinogen, Factor XIII and mature thrombin under conditions such that thrombin clotting activity is inhibited; and ii) applying a preparation resulting from step (i) to the body site under conditions such that thrombin clotting activity is restored and the fibrin sealant is formed.

In another embodiment, the present invention relates to a method of effecting the formation of fibrin sealant at a body site comprising: i) forming a suspension comprising a first phase which comprises fibrinogen and Factor XIII and a second phase which comprises thrombin, and ii) applying the suspension to the body site under conditions such that mixing of the fibrinogen, Factor XIII and thrombin is effected so that the fibrin sealant is formed.

In a further embodiment, the present invention relates to a kit for use in the preparation of a fibrin sealant. The kit includes an applicator comprising: i) a container means having disposed therein a solution comprising fibrinogen, Factor XIII and mature thrombin; and ii) an outlet means operably connected to said container means.

DETAILED DESCRIPTION OF INVENTION

The present invention relates to a method of delivering the components of a fibrin sealant (calcium, mature thrombin (as opposed to prothrombin) and the plasma-derived fibrinogen/Factor XIII precipitate) to a body site in a manner such that clot formation is effected, and to a kit suitable for use in such a method. (The term "body site" as used herein includes the tissue in the area of a wound or incision as well as implantable tissues or components to be inserted into the area, e.g., vascular prostheses, bone or collagen pads.) In the description that follows, it will be appreciated that a combination of isolated forms of fibrinogen and Factor XIII can be used in place of the plasma-derived precipitate.

In the method of the present invention, a fibrinogen/Factor XIII-enriched precipitate and mature thrombin are mixed together under conditions such that thrombin and/or Factor XIII are/is inactivated (or under conditions such that thrombin is present in an active form but is rendered unavailable, as in the calcium depletion embodiment described below) and clotting thereby prevented. The mixture is then delivered to the body site under conditions such that the enzyme activity is restored (or thrombin availability restored).

In one embodiment, the mixture of thrombin and fibrinogen/Factor XIII precipitate is prepared in a low pH buffer (the clotting of fibrinogen by thrombin being inhibited by low pH (less than 5.5)). In this embodiment, thrombin activity is restored and clotting rapidly initiated upon neutralization of the mixture with a pharmaceutically acceptable buffer, or alternatively, upon contact of the mixture with the patient's own body fluids. In this embodiment, the fibrinogen/Factor XIII precipitate can be prepared at a low pH or, alternatively, a low pH buffer can be used to dissolve the plasma precipitate and the lyophilized thrombin. In either case, the mixture can be transferred to a delivery container (such as a spray bottle or syringe) and applied to the body site directly, if conditions are such that the patient's body fluids are sufficient to increase the pH to a point where clotting occurs. Where conditions are such that the patient's body fluids are not sufficient to raise the pH of the precipitate/thrombin mixture to a point where thrombin activity is restored, a delivery device can be used that is designed such that, as the acidic mixture passes out of the device, it is contacted with buffer salts coated on an interior portion of the device. The buffer salts are selected such that when contact is made with the acidic mixture, dissolution occurs with the result that the pH is raised to a point where clotting takes place. For example, a syringe can be used as the delivery device (applicator), where the syringe is fitted with a disposable tip, the interior surface of which is coated with appropriate buffer salts. As the acidic mixture passes through the coated tip, the buffer (in the form, for example, of crystals or a gel) neutralizes the acidic mixture, thus restoring thrombin activity and effecting the formation of a clot at the desired site. Should clot formation occur in the tip, the tip can simply be removed and a new coated tip attached.

In another embodiment, the fibrinogen and Factor XIII precipitate/thrombin mixture can be prepared in a buffer that is depleted of calcium. Rapid clot formation requires the presence of calcium ions; thus, if the calcium is removed, fibrin polymerization is inhibited (see Carr et al Biochem J. (1986) 239:513; Kaminski et al J. Biol. Chem (1983) 258:10530; Kanaide et al (1982) 13:229). Calcium chelators (compounds such as sodium citrate or ethylenediaminetetraacetic acid, which tightly bind calcium and make it inacces'sible) can be added to the solution used to precipitate the fibrinogen and Factor XIII and/or the dissolving buffer. To restore activity, the container (for example, a syringe) can be attached to a disposable sterile tip, the interior surface of which is coated internally with sufficient calcium salt to saturate the chelator. As the free calcium concentration increases upon passage of the mixture through the tip, clotting is effected at the body site.

In a further embodiment, the clotting activity of thrombin, in the precipitate/thrombin mixture, can be inhibited using a photosensitive inhibitor. For example, light sensitive cinnamoyl derivatives can be used to inactivate thrombin, at room temperature in the absence of light, for more than 26 hours (Turner et al J. Am. Chem. Soc. 109: 1274-1275 (1987); Turner et al J. Am. Chem. Soc. 110: 244-250 (1988)). These same thrombin inhibitor complexes can generate active thrombin within 1-2 seconds of irradiation (low intensity. These inhibitors are known to form acyl-enzyme complexes involving the active site serine hydroxyl (SER 195). Upon irradiation, the cinnamoyl derivative undergoes photoisomerization to release coumarin and regenerate the active serine hydroxyl. Since coumarin derivatives are not good thrombin inhibitors, this photocyclization reaction effectively removes inhibitor from the enzyme solution. Thus, a solution of the fibrinogen/Factor XIII-enriched precipitate can be mixed with lyophilized inhibitor thrombin complex in a dark environment (such as an opaque or colored syringe or container) and delivered to the wound site. Activation of the enzyme and thus clot formation occurs upon delivery to the wound due to the exposure of the solution to normal room light. Alternatively, activation can be controlled by a light source, for example, one built directly into the applicator, so that variations in lighting conditions will not result in variable clotting times.

In yet another embodiment, premature clot formation can be prevented prior to delivery of the fibrinogen and Factor XIII/thrombin mixture by physically separating the thrombin from the fibrinogen/Factor XIII precipitate. In this embodiment, physical separation is effected using a two-phase system. Liquids suitable for use in this embodiment are non-miscible and readily separable into two phases. The two phases are mixed into a suspension before each application and delivered to the wound. Where conditions are such that the patient's body fluids extract the soluble component of the non aqueous phase, mixing occurs at the body site and clotting is thus initiated. If conditions will not elicit proper mixing of components, a delivery device can be used that is designed such that, as the suspension passes out of the device, it is contacted with a solubilizing agent coated on an interior portion of the device. The solubilizing agent is selected such that when contact is made with the suspension, dissolution occurs with the result that mixing occurs to a degree where clotting takes place. For example, a syringe is fitted with a disposable tip, the interior surface of which is coated with an appropriate phase transfer agent(s). As the suspension passes through the coated tip, the phase transfer agent (in the form, for example, of crystals) assists in the mixing process, thus allowing clot formation. Should clot formation occur in the tip, the tip can simply be removed and a new coated tip attached.

The present invention also relates to a kit suitable for use in the above-described method of delivering fibrin sealant components to a wound site. In a preferred embodiment the kit includes an applicator designed so as to permit mixing of the fibrinogen/Factor XIII precipitate and thrombin in a single system. The applicator can be one that permits the application at the body site of, for example, a film, or a thin line of the components of fibrin sealant. Alternatively, a pump or aerosol spray applicator can be used.

As suggested above, the applicator can, for example, take the form of a glass or plastic syringe with disposable tips. The shape of the tip will determine the form in which the components are delivered. A tip with a flat, broad end can be used to deliver a thin wide streak of fibrin sealant whereas a narrow tubular end can be used to deliver a round thread of sealant. Applying pressure to force the mixture through a tip constricted with, for example, a mesh screen can be used to produce a spray, resulting in a fine glaze of fibrin sealant. In another embodiment, particularly suitable for use with the above-described photosensitive thrombin inhibitor, the applicator can take the form of a pump or aerosol spray device having a built-in light source situated such that, as the sealant components exit the device, they are irradiated with the light. The wavelength of light used would depend on the photosensitizer.

The kit can be structured so as to include individual storage containers for the separate fibrin sealant components. The kit can also include one or more other storage containers disposed within which are any necessary reagents including solvents, buffers, etc.

The present invention will be understood in greater detail by reference to the following nonlimiting

EXAMPLE

A precipitate containing fibrinogen and Factor XIII was prepared as follows:

Four hundred fifty microliters of a stock 1 M zinc sulfate solution were added to 5 ml of anticoagulated (citrate phosphate dextrose adenine (CPDA-1)) human plasma. The solution was mixed well without vortexing and centrifuged at 2,000 to 9,000 g for 5 minutes. The supernatant was decanted and discarded.

Inhibition of clotting and reactivation was achieved by any of the following methods A. Acid Inhibition—Lyophilized bovine thrombin was dissolved in citrate buffer (500 mM citric acid, 150 mM NaCl, and 20mM EACA, pH 4.5) to a final concentration of 100 U/ml. Precipitated fibrinogen was dissolved in Trisouffer (50 mM Tris, 250 mM sodium citrate, 150 mM sodium chloride, 50 mM Arginine (Arg), and 20 mM $\epsilon$-amino-caproic acid (EACA), pH 7.4) to a concentration of approximately 15.0 mg/ml. This fibrinogen stock was then diluted 25-fold in citrate buffer. The clotting time for 200 microliters of this fibrinogen solution plus 100 microliters thrombin exceeded 90 seconds in a Becton Dickinson BBL Fibrosystem fibrometer under standard conditions indicating no clot formation. Addition of 70 microliters of 1N sodium hydroxide resulted in clot formation in 3.8 seconds (average of 10 samples).

The following procedures can be used for application to a wound site:

Where body fluids are sufficient to neutralize the acidic mixture of precipitate and thrombin, the mixture can be applied directly to the wound site. Alternatively, the delivery device can be connected to disposable tips coated internally with a neutralizing salt or gel (e.g. Tris). Neutralization of the acidic solution by the buffer salts activates thrombin nd restores clotting activity.

B. Chelator Inhibition—Precipitated fibrinogen and lyophilized bovine thrombin were dissolved in Tris buffer (50 mM Tris, 250 mM sodium citrate, 150 mM sodium chloride, 50 mM Arg, and 20 mM EACA, pH 7.4) to a concentration of approximately 15.0 mg/ml and 100 U/ml, respectively. The fibrinogen stock solution was then diluted 25-fold in Tris buffer containing 500 mM sodium citrate. The clotting time for 200 microliters of this fibrinogen solution plus 100 microliters thrombin exceeded 90 seconds in a Becton Dickinson BBL fibrosystem fibrometer under standard conditions. Addition of 50 microliters of a 1M $CaCl_2$ solution resulted in clot formation in 1.8 seconds (average of 10 samples).

The following procedure can be used for application to a wound site:

The delivery device is connected to disposable tips coated internally with a calcium salt or gel. As the mixture passes through the tip, the molar excess of calcium saturates the chelator and clotting is thereby promoted.

C. Photosensitive Inhibition—In the absence of light, a 5 to 20-fold excess of 4-amidino-phenyl-2-hydroxy-4-diethylamino-alpha-methylcinnamate hydrochloride (Porter et al, J. Amer. Chem. Soc. 111:7616 (1989)) was added to thrombin in buffer (approximately 100 U/ml in 50 mM Tris, 250 mM sodium chloride, 250 mM sodium citrate, 20 mM EACA, 50 mM arginine (or urea), pH 7.4, final methanol concentration <10%). The inhibitaion was allowed to proceed for at least 1 hour at room temperature.

A minimal quantity of this solution was used to dissolve the precipitated fibrinogen/Factor XIII. This sealant required approximately 2 to 3 minutes illumination under standard operating lights to clot completely, whereas a sample mixture kept in the dark did not clot after 90 min.

The following procedures can be used for application to a wound site:

The photosensitive inhibitor-thrombin complex can be mixed with the precipitated fibrinogen/Factor XIII in a colored delivery device that does not transmit light of the activating wavelengths. Delivery of the mixture to an illuminated wound site results in clot formation.

D. Two Phase Suspension—Lyophilized bovine thrombin is dissolved in an emulsifying agent to a final concentration of about 100 U/ml. Precipitated fibrinogen/Factor XIII is dissolved in a minimal volume of buffer (50 mM Tris, 150 mM sodium chloride, 250 mM sodium citrate, 20 mM EACA, 50 mM Arg, pH 7.4). A suspension of the immiscible liquids is formed. On a wound surface, body fluids may be sufficient to dissolve both components and promote proper mixing and clot formation.

The entire contents of each of the references cited above are hereby incorporated by reference.

While the present invention has been described in some detail for purposes of clarity and understanding, it will be clear to one skilled in the art from a reading of this disclosure that various changes can be made in form and detail without departing from the true scope of the invention.

What is claimed is:

1. A method of effecting the formation of fibrin sealant at a body site comprising:
   i) mixing, in a container means, an aqueous solution comprising fibrinogen, Factor XIII and mature thrombin under conditions such that thrombin clotting activity is inhibited; and
   ii) applying a preparation resulting from step (i) to said body site under conditions such that thrombin clotting activity is restored and said fibrin sealant is formed;

wherein step (i) is carried out at a pH of less than 5.5, whereby thrombin clotting activity is inhibited.

2. The method according to claim 1 wherein, in step (ii), the pH of said preparation resulting from step (i) is increased such that thrombin clotting activity is restored.

3. The method according to claim 2 wherein the pH of said preparation resulting from step (i) is increased upon contact of said preparation with body fluids of said patient present at said body site.

4. The method according to claim 2 wherein, in step (ii), the pH of said preparation resulting from step (i) is increased upon contact with a buffered capable of increasing the pH.

5. A method of effecting the formation of fibrin sealant at a body site comprising:
   i) mixing, in a container means, an aqueous solution comprising fibrinogen, Factor XIII and mature thrombin under conditions such that thrombin clotting activity is inhibited; and
   ii) applying a preparation resulting from step (i) to said body site under conditions such that thrombin clotting activity is restored and said fibrin sealant is formed;

wherein said solution of step (i) includes an amount of a photosensitive inhibitor of thrombin clotting activity sufficient to inhibit thrombin clotting activity.

6. The method according to claim 5 wherein, in step (ii), said preparation resulting from step (i) is irradiated with light of a wavelength that inactivates said photosensitive inhibitor, whereby thrombin clotting activity is restored.

* * * * *

UNITED STATES PATENT AND TRADEMARK OFFICE
CERTIFICATE OF CORRECTION

PATENT NO. : 5,219,328
DATED : June 15, 1993
INVENTOR(S) : Brenda S. Morse and A. Denise Turner It is certified that error appears in the above-identified patent and that said Letters Patent is hereby corrected as shown below:

Title page of patent, item [75], change "Brenda S. Morse, Chamblee; A. Denise Turner, Dunwoody; Robert T. McNally, Marietta, all of Ga." to --Brenda S. Morse, Chamblee; A. Denise Turner, Dunwoody, both of Ga.--.

Signed and Sealed this

Twenty-first Day of June, 1994

Attest:

BRUCE LEHMAN

Attesting Officer   Commissioner of Patents and Trademarks